US009463019B2

(12) United States Patent
Metzinger et al.

(10) Patent No.: US 9,463,019 B2
(45) Date of Patent: Oct. 11, 2016

(54) TROCAR SITE CLOSURE ASSEMBLY

(71) Applicant: University of Louisville Research Foundation, Inc., Louisville, KY (US)

(72) Inventors: Daniel S. Metzinger, Louisville, KY (US); Robert S. Keynton, Louisville, KY (US); Scott D. Cambron, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 107 days.

(21) Appl. No.: 14/279,765

(22) Filed: May 16, 2014

(65) Prior Publication Data

US 2014/0343603 A1    Nov. 20, 2014

Related U.S. Application Data

(60) Provisional application No. 61/824,247, filed on May 16, 2013.

(51) Int. Cl.
*A61B 17/08* (2006.01)
*A61D 1/00* (2006.01)
*A61B 17/00* (2006.01)

(52) U.S. Cl.
CPC .......... *A61B 17/08* (2013.01); *A61B 17/0057* (2013.01); *A61B 2017/00592* (2013.01);
(Continued)

(58) Field of Classification Search
CPC A61B 17/0057; A61B 17/08; A61B 17/081; A61B 17/083; A61B 2017/00575; A61B 2017/00579; A61B 2017/00584; A61B 2017/00592; A61B 2017/0061; A61B 2017/00619; A61B 2017/00623; A61B 2017/00637; A61B 2017/00659
See application file for complete search history.

(56) References Cited

U.S. PATENT DOCUMENTS 5,397,331 A    3/1995 Himpens et al.
5,476,470 A   12/1995 Fitzgibbons, Jr.
(Continued)

FOREIGN PATENT DOCUMENTS

RU         2103929 C1    10/1998
RU           70113 U1     1/2008
WO    WO 2012/015678 A1   2/2012

OTHER PUBLICATIONS

Moreno-Sanz, Carlos, et al, "Prevention of trocar site hernias: description of the safe port plug technique and preliminary results," Surg. Innov., vol. 15, No. 2, Jun. 2008, pp. 100-104.
(Continued)

*Primary Examiner* — Melanie Tyson
(74) *Attorney, Agent, or Firm* — Bingham Greenebaum Dell LLP; James C. Eaves, Jr.; Brian W. Chellgren

(57) ABSTRACT

Embodiments of this invention relate to trocar site closures including a head with a plurality of arm receiving passages therethrough, an arm received by each of the passages, each passage having a discontinuity which allows each arm to be pulled inward but deters outward movement, and each arm having a grappling portion. The head and arms are inserted into a patient wound, such as a trocar site. The arms engage with tissue surrounding the wound. A pulling force is exerted on the arm proximal ends, drawing the distal ends of the arms toward the head and at least partially closing the wound. The head and at least a portion of the arms remain in the patient, and are preferably made of a biocompatible material. Embodiments of this invention also relate to an insertion device used to insert the closure into the wound and at least partially close the wound.

19 Claims, 8 Drawing Sheets

(52) U.S. Cl.
CPC ............... *A61B2017/00619* (2013.01); *A61B 2017/00623* (2013.01); *A61B 2017/00637* (2013.01); *A61B 2017/081* (2013.01)

(56) References Cited

U.S. PATENT DOCUMENTS

| | | | |
|---|---|---|---|
| 8,323,312 B2 | 12/2012 | Clark | |
| 9,011,485 B2 † | 4/2015 | Klein | |
| 9,039,734 B2 † | 5/2015 | Klein | |
| 2003/0171764 A1 | 9/2003 | Debbas | |
| 2008/0281339 A1* | 11/2008 | Kirschman | A61B 17/688 606/151 |
| 2009/0182352 A1* | 7/2009 | Paz | A61B 17/0643 606/143 |
| 2010/0179576 A1 | 7/2010 | Halevy | |
| 2011/0144661 A1 | 6/2011 | Houser et al. | |
| 2011/0251638 A1 | 10/2011 | Klein et al. | |
| 2012/0022586 A1 | 1/2012 | Whitman et al. | |
| 2012/0316594 A1 | 12/2012 | Palese | |
| 2014/0200597 A1 † | 7/2014 | Klein | |

OTHER PUBLICATIONS

W.L. Gore & Associates, Inc. "Shaping Natural Healing for Hernia Repair," [Brochure], AN2984-EN2, May 2011.
International Preliminary Report on Patentability issued in PCT/US2014/038369. Nov. 17, 2015.

\* cited by examiner
† cited by third party

TROCAR SITE CLOSURE ASSEMBLY

This application claims the benefit of U.S. Provisional Patent Application Ser. No. 61/824,247, filed 16 May 2013, entitled Trocar Site Closure Device, by Daniel S. Metzinger, Robert S. Keynton, and Scott D. Cambron, the provisional application incorporated herein by reference.

FIELD OF THE INVENTION

Disclosed herein are trocar site closures. The closures may include an assembly with a head component to at least partially block a trocar site opening in the body. They also may include a tissue engaging mechanism and a locking mechanism. Closures are taught comprising a head with a plurality of arm receiving passages therethrough, an arm received by each of the arm receiving passages, each arm receiving passage having a discontinuity which allows each arm to be pulled inward but deters outward movement, and each of the arms having a grappling portion. The head and arms are inserted into a patient wound, such as a trocar site. The arms engage with tissue surrounding the wound. A pulling force is exerted on the arm proximal ends, drawing the distal ends of the arms toward the head and at least partially closing the wound. The head and at least a portion of the arms remain in the patient, and these elements remaining in the patient are preferably made of a biocompatible material, such as, for example, a bio-absorbable material and/or a bio-degradable material. Also disclosed herein is an insertion device which can be used to assist in inserting a closure into the patient wound and at least partially closing the wound.

BACKGROUND OF THE INVENTION

Laparoscopy has gained widespread acceptance as a replacement for open abdominal surgery because of better postoperative outcomes such as less pain, faster recovery, and lower risk of incisional hernias. Laparoscopy utilizes small incisions in the abdomen (or other body part) to insert a trocar, a medical instrument with a sharply pointed end, often three sided, which is used inside a hollow cylinder (cannula) to introduce the trocar into blood vessels or body cavities. In the industry, the cannula and pointed instrument together, the pointed instrument alone, or the cannula alone may be referred to as a trocar. The pointed instrument is often passed inside a central channel of the cannula, forming an opening, and is then removed. The central channel of the cannula then functions as a portal for the subsequent placement of other devices, such as a chest drain, port, intravenous cannula, etc. Trocar sites are the openings made in a patient's body by the trocar.

Laparoscopy allows for intricate procedures to be performed, however larger trocars are often required to execute complex surgeries. Use of larger trocars requires larger trocar sites, which results in an increase in the possibility of complications following surgery. These complications can include incisional bowel herniation (hernia) and small bowel obstruction (SBO).

The closure of laparoscopic trocar sites is helpful in reducing such complications. The risk of hernia following laparoscopic surgery (i.e. trocar site hernia or TSH) has been known since 1967. Despite this length of time, data is still sparse and based mostly on retrospective studies with a short and poorly defined follow-up. Surgical approaches and patient-related co-morbidity have also been suggested as risk factors for development of TSH. Controversies also exist regarding both prevention and repair of TSH. Trocar complications occur in approximately 1% to 6% of patients. Herniation associated with laparoscopic trocar sites can occur with incisions as small as 3 mm. Studies have recommended that all 10 and 12 mm trocar sites in adults and all 5 mm port sites in children be closed, incorporating the peritoneum into the fascial closure. One study found TSHs to have an incidence of 0.23% at 10 mm port sites and 1.9% at 12 mm port site. This incidence markedly increases to 6.3% for obese patients with a body mass index (BMI) greater than 30.

A number of techniques and devices have been developed to facilitate trocar site closure. Surgical techniques using small retractors and specially curved needles are available. However, using these pose some degree of technical difficulty and can be ineffective with thicker abdominal walls. There are also a number of needle-based devices that puncture the fascia by inserting the needle into the skin incision, piercing the fascia and peritoneum along with suture material, and bringing it out on the other side of the trocar site. However, most of the devices on the market are cumbersome to use, require a learning curve for proficient use, and cause trocar site pain due to the incorporation of the peritoneum into the closure.

SUMMARY

Disclosed herein are trocar site closures. The closures may include an assembly with a head component to at least partially block a trocar site opening in the body. They also may include a tissue engaging mechanism and a locking mechanism. Closures are taught comprising a head with a plurality of arm receiving passages therethrough, an arm received by each of the arm receiving passages, each arm receiving passage having a discontinuity which allows each arm to be pulled inward but deters outward movement, and each of the arms having a grappling portion. The head and arms are inserted into a patient wound, such as a trocar site. The arms engage with tissue surrounding the wound. A pulling force is exerted on the arm proximal ends, drawing the distal ends of the arms toward the head and at least partially closing the wound. The head and at least a portion of the arms remain in the patient, and these elements remaining in the patient are preferably made of a biocompatible material, such as, for example, a bio-absorbable material and/or a bio-degradable material. Also disclosed herein is an insertion device which can be used to assist in inserting a closure into the patient wound and at least partially closing the wound.

Embodiments disclosed herein pertain to trocar site closures including a head with plurality of arms each having a grappling portion for grasping, holding, or cinching tissue surrounding a trocar site, which facilitate at least partially closing the opening in the patient's body. The risk of TSH can be reduced by leaving the head of the trocar site closure within the patient's body. This can block tissue from entering the trocar site. Additionally taught is an insertion device, where a portion of a closure engages or abuts an opening at the insertion end of the body of the insertion device. The insertion device assists with insertion of the closure and with at least partial closing of the body opening.

More specifically, disclosed herein is a trocar site closure, comprising: a head having a plurality of arm receiving passages therethrough, each of the plurality of arm receiving passages having a discontinuity therein; a plurality of arms each having a distal end and an opposed proximal end and each arm having a grappling portion; each arm received by one of the arm receiving passages; and where the discontinuity in each arm receiving passage permits movement of the arm received when the arm is pulled from its proximal end, but where the discontinuity in each arm receiving passage deters movement of the arm received when the arm is pulled from its distal end. Preferably, each arm receiving passage is from an exterior opening in the head to an interior opening in the head and each arm received in the arm receiving passage has a portion terminating in its distal end extending from the exterior opening and a portion terminating in its proximal end extending from the interior opening. Also preferably, each discontinuity is a ramp which slopes upward from a location toward the exterior opening in the head to a location toward the interior opening in the head. In some embodiments, the arms have a plurality of openings therein, where at least one of the openings can engage the ramp contained in the passage through which the arm passes.

Even further, the head of the trocar site closure can have a top portion and a top open end, where the arm portion terminating in the proximal end extending from the interior opening extends further through said top open end. This head top portion can removably abut an insertion end of a body of an insertion device and the said arm portions extending through the top open end and terminating in the proximal end are removably received within the insertion end of said body. The insertion device includes a control mechanism operably linked to the arm portions removably received within the insertion end of the body such that these arm portions can be pulled upward in the body of the insertion device to decrease a length of the arms extending from the head exterior openings to their distal ends.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
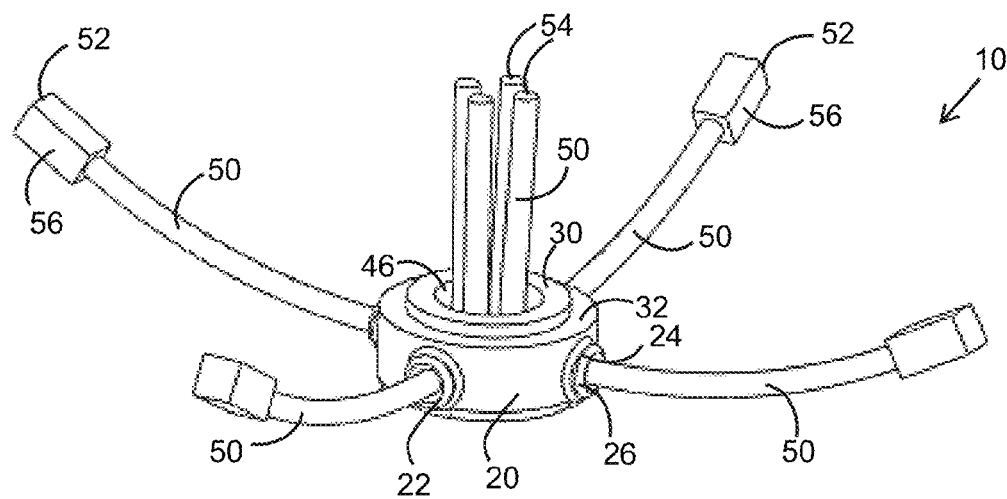
FIG. 1 is a perspective view of a first embodiment of a trocar site closure.
Figure 2:
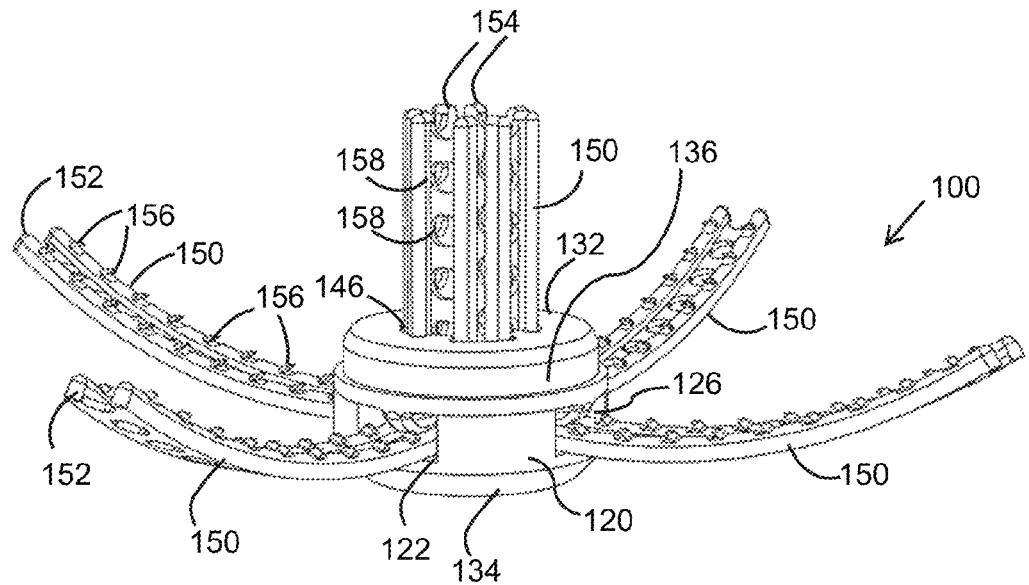
FIG. 2 is a perspective view of a second embodiment of a trocar site closure.

An opening in a patient formed by a trocar is referred to as a trocar site. Two embodiments, 10 and 100, of a trocar site closure are shown in FIGS. 1 and 2. Closures 10, 100 each include a head 20, 120 and a plurality of arms 50, 150.

In closure 10, as seen in FIGS. 1 and 3-12, head 20 has a plurality of arm receiving passages 22, each extending from an exterior opening 26 in head 20 to an interior opening 28 in head 20. Each passage 22 receives an arm 50, each arm 50 having a distal end 52 and an opposed proximal end 54. Each arm 50 has a grappling portion 56. Portion 56 may be at the distal end 52 and/or along a portion of the length of arm 50. Each passage 22 includes a discontinuity 24 which permits the arm 50 received by passage 22 to move in an inward direction as a pulling force is exerted on the proximal end 54 of the arm 50. That results in the length of the arm 50 between the distal end 52 and the corresponding exterior opening 26 decreasing as such pulling force is applied. However, the discontinuity 24 serves to deter, and preferably prevent, lengthening of the portion of the arm 50 that extends outwardly from the corresponding exterior opening 26 in the event a distal force is applied to said portion of the arm 50 (e.g., a pulling force exerted on the distal end 52 of the arm 50 in a direction away from the head 20). As is explained hereinafter, the arm 50 may or may not have components which work with the discontinuity 24 to cause this result. Head 20 is shown with a ring portion 30 and a top portion 32. Head 20 also has a top open end 46.

Figure 3:
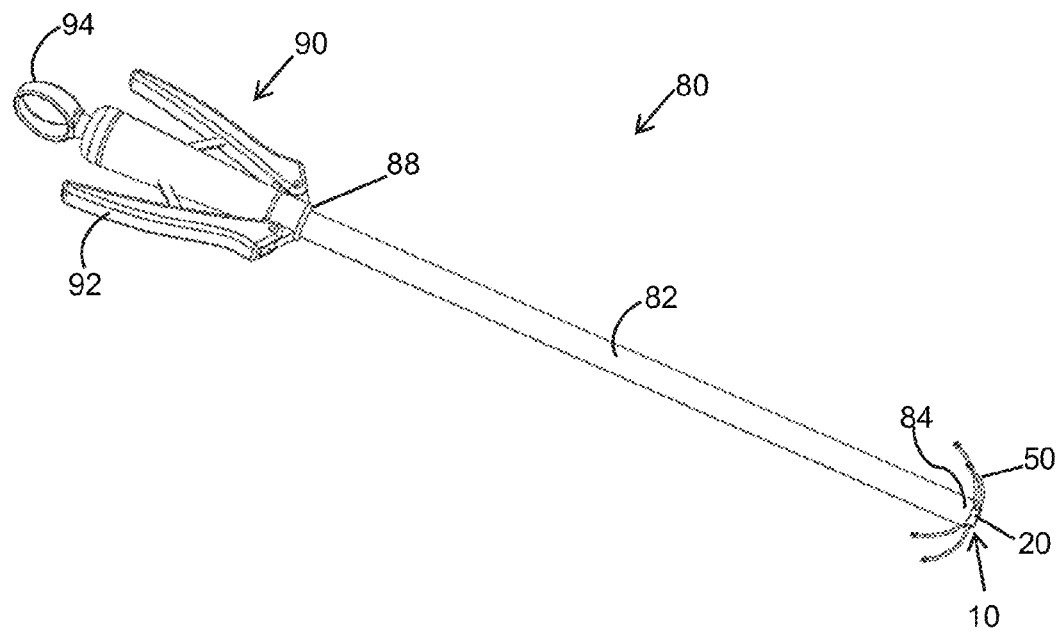
FIG. 3 is a perspective view of an insertion device with the trocar site closure of the first embodiment.

An insertion device, such as the insertion device 80 shown in FIG. 3 can be used to insert the trocar site closure 10 through a central opening 4 in a trocar 2 and into a patient's body opening 8 through fascial layer 6 which results from the insertion of the trocar 2 into the patient's body. Insertion device 80 is shown having a body 82 with an insertion end 84 and a control end 88. As further illustrated in FIG. 3, closure 10 is shown at the insertion end 84 of insertion device 80. At control end 88 is control mechanism 90, including grips 92 and ring 94.

Insertion device 80 with control mechanism 90 can be used to insert the closure 10 through a trocar 2 opening 4 into a wound or body opening 8 of a patient. Thereafter, the control mechanism 90 can be used to attach the grappling portions 56 of arms 50 to the facial layer 6 and, in turn, utilized to retract the arms 50 to at least partially close the opening 8. This is explained further with reference to FIGS. 1 and 3-12, and the process is illustrated sequentially in FIGS. 5-12.

Figure 5:
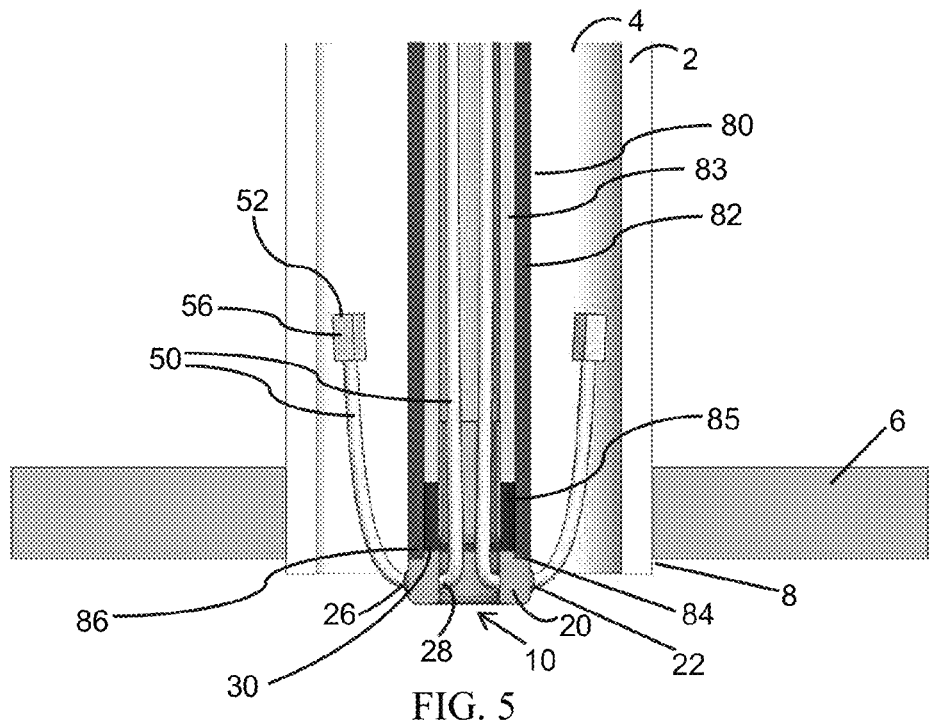
FIGS. 5-12 illustrate use of the insertion device with the trocar site closure of the first embodiment.

In the illustration of FIG. 5, a portion of trocar 2 is shown inserted into the facial layer 6 and body opening 8. Trocar 2 is shown with a central opening 4, which receives closure 10 and a portion of insertion device 80. The top ring portion 30 of head 20 is received in opening 86 at insertion end 84 of insertion device 80. Body 82 receives a movable inner sleeve 83 with an attached shearing member 85, having a diameter smaller than that of sleeve 83. The inner sleeve 83 is received in body 82 such that the shearing member 85 is positioned toward the insertion end 84 of body 82. A portion of head 20 is shown with each passage 22 having an exterior opening 26 and an interior opening 28. An arm 50 is shown inserted in each passage 22 with the distal end 52 and grappling portion 56 of the arm 50 extending from exterior opening 26 and away from the head 20, shown in an upward direction. The portion of arm 50 which extends proximally and in an upward direction with respect to interior opening 28 is positioned within inner sleeve 83 and body 82.

Figure 6:
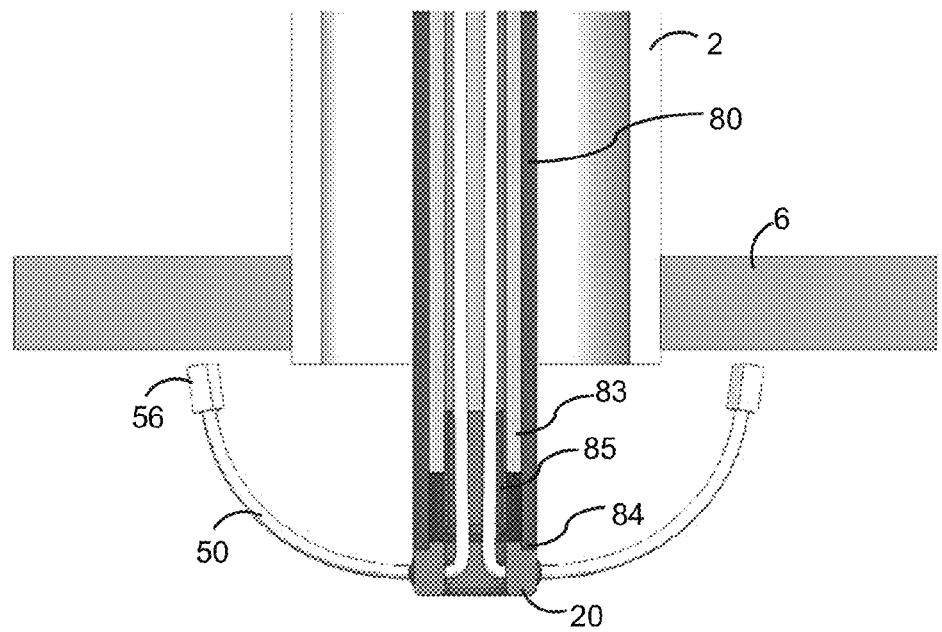

In FIG. 6, insertion device 80 is shown further extended through the central opening 4 such that that insertion end 84 of device 80 and head 20 of closure 10 have advanced beyond the distal end of the trocar 2, thereby permitting the portions of the arms 50 that extend distally from exterior openings 26 to release from within central opening 4 of the trocar 2 and to expand.

Figure 7:
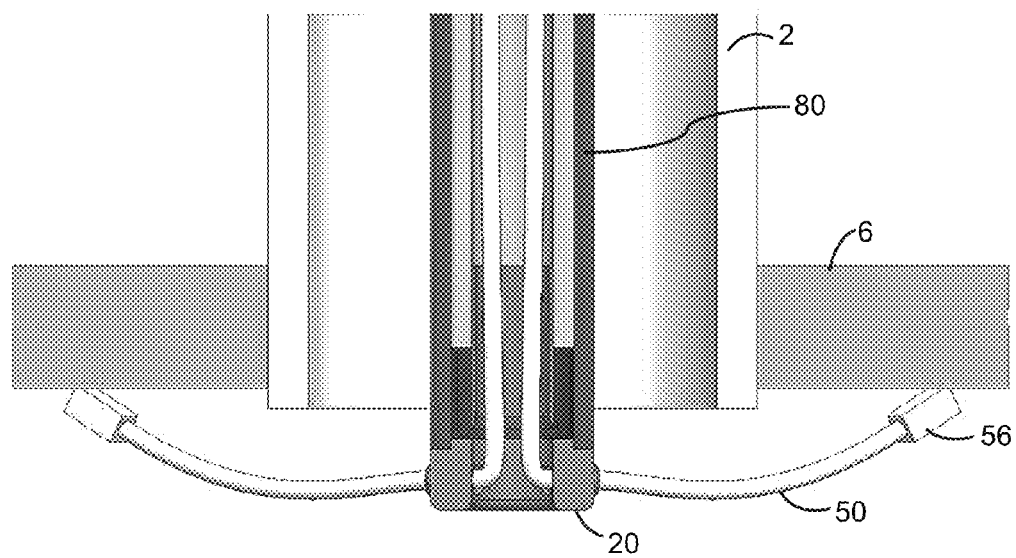
Figure 8:
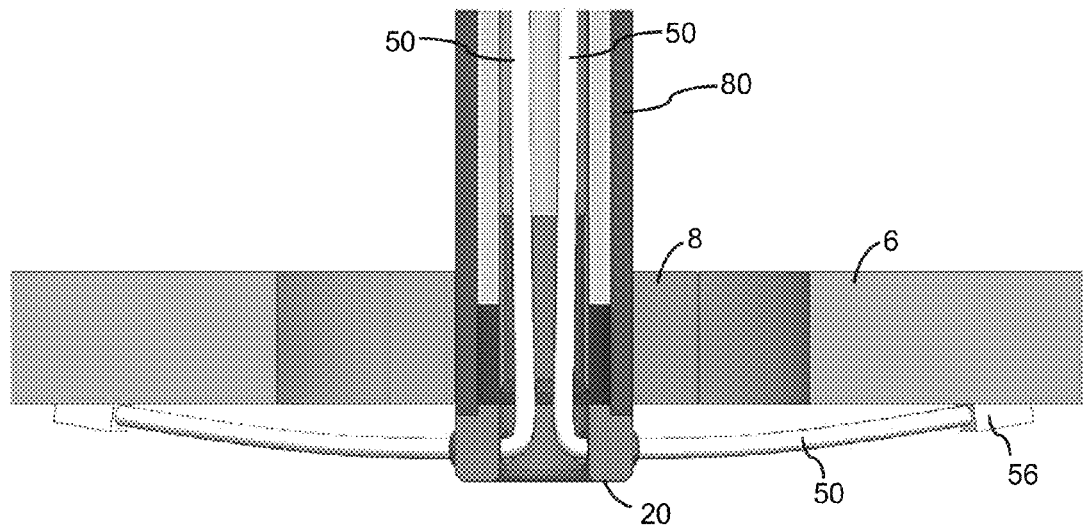

In FIG. 7, the insertion device 80 has been pulled upward slightly so that the grappling portions 56 of arms 50 have started to engage the fascial layer 6. In FIG. 8, the insertion device 80 has been pulled further slightly upward so that the grappling portions 56 are more engaged with the fascial layer 6. Additionally, the trocar 2 has been removed, leaving body opening 8.

Figure 9:
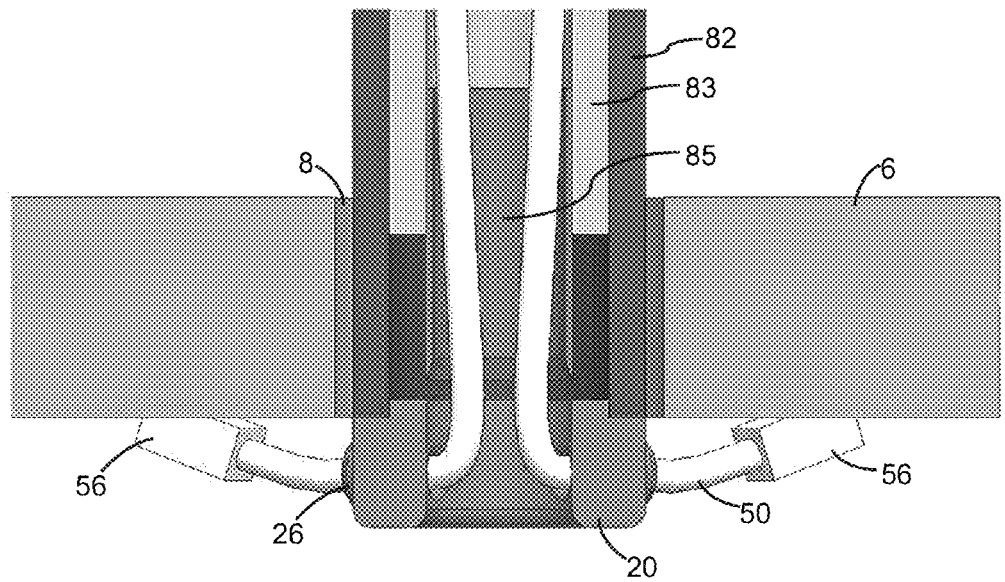

In FIG. 9, the arms 50 have been pulled upward at their proximal ends 54 using the control mechanism 90. As seen, the length of each arm from the exterior opening 26 to the grappling portion 56 is much less in FIG. 9 than in FIG. 8. Also, the engagement of the grappling portions 56 with the fascial layer 6 has resulted in the body opening 8 being much reduced in size in FIG. 9 as compared with that shown in FIG. 8. As further shown in FIG. 9, body opening 8 is sufficiently closed.

Figure 10:
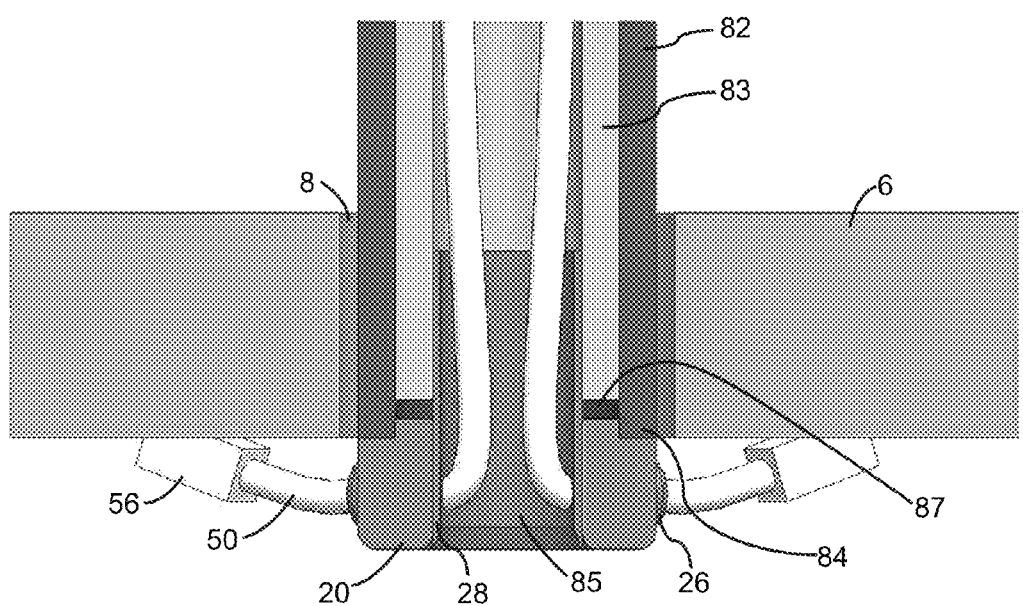
Figure 11:
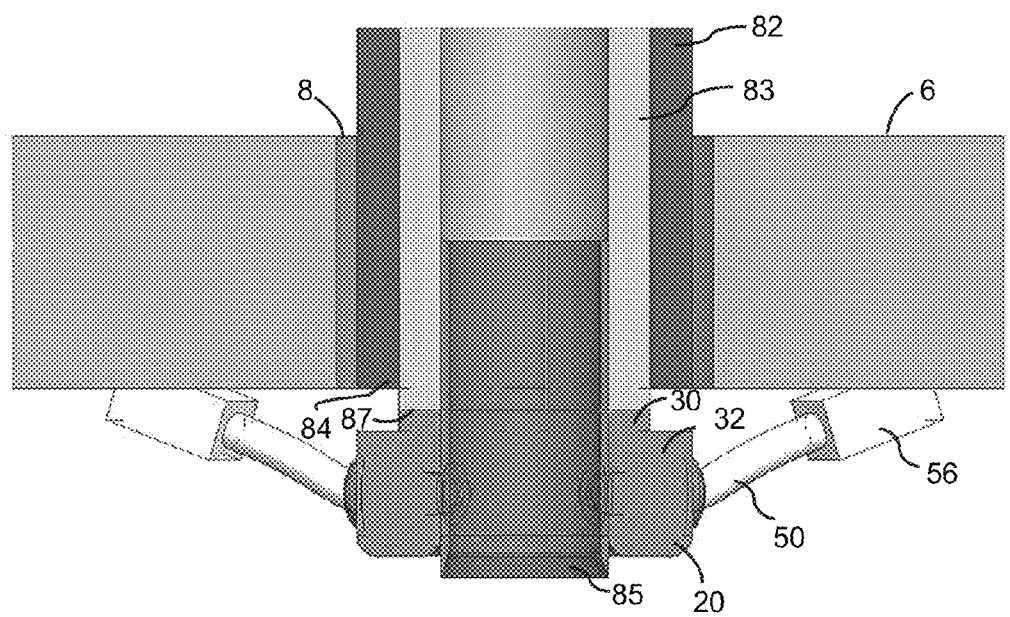

In FIG. 10, inner sleeve 83 with attached shearing member 85 has moved downward within body 82 such that shearing member 85 has severed portions of arms 50 at the interior opening 28 of head 20. In FIG. 11, the portions of arms 50 severed as in FIG. 10 have been removed from inside sleeve 83. As compared to FIG. 10, in FIG. 11, inner sleeve 83 has been moved further downward so that the end 87 of inner sleeve 83 engages the ring portion 30 of head 20 and head 20 has been detached from insertion end 84 of body 20.

Figure 4:
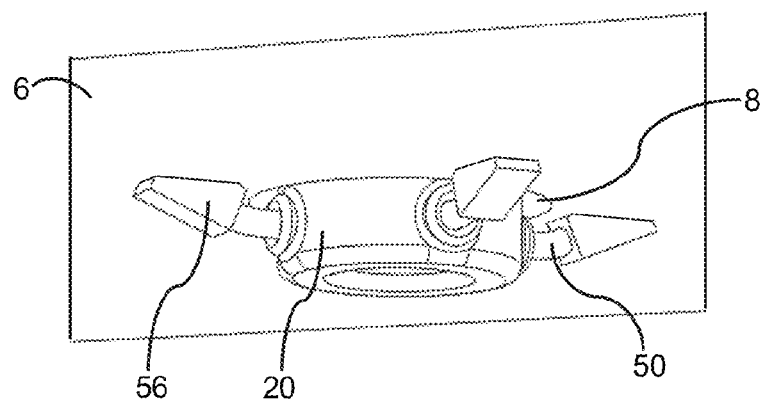
FIG. 4 depicts the head and arm portions of the first embodiment left within a body cavity after insertion of the trocar site closure and at least partial closure of the body opening.
Figure 12:
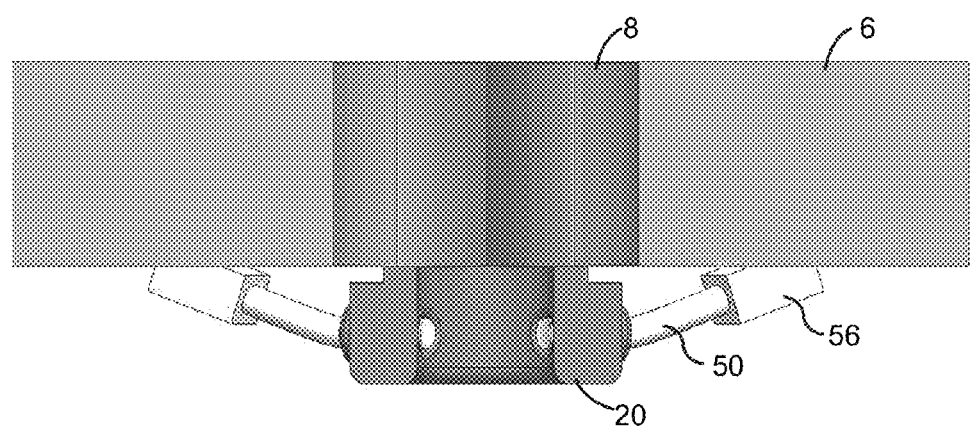

In FIG. 12, the insertion device 80 has been removed from body opening 8, leaving the head 20 and a portion of the arms 50 within the body. Grappling portions 56 engage the fascial layer 6 and keep the opening 8 at least partially closed. It is envisioned that these portions will remain in the body as they are preferably made of biocompatible material. FIG. 4 is a similar view to the illustration of FIG. 12.

Figure 13:
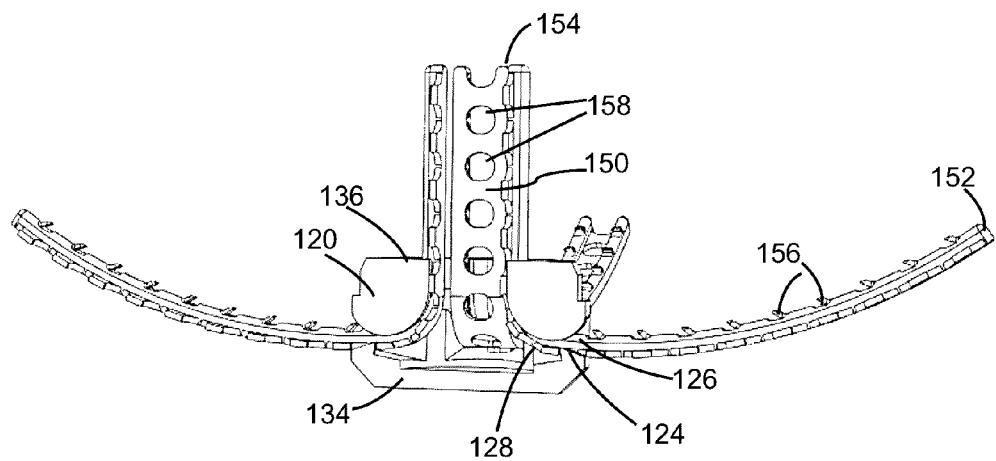
FIG. 13 is a cross-section view of the trocar site closure of FIG. 2.
Figure 14:
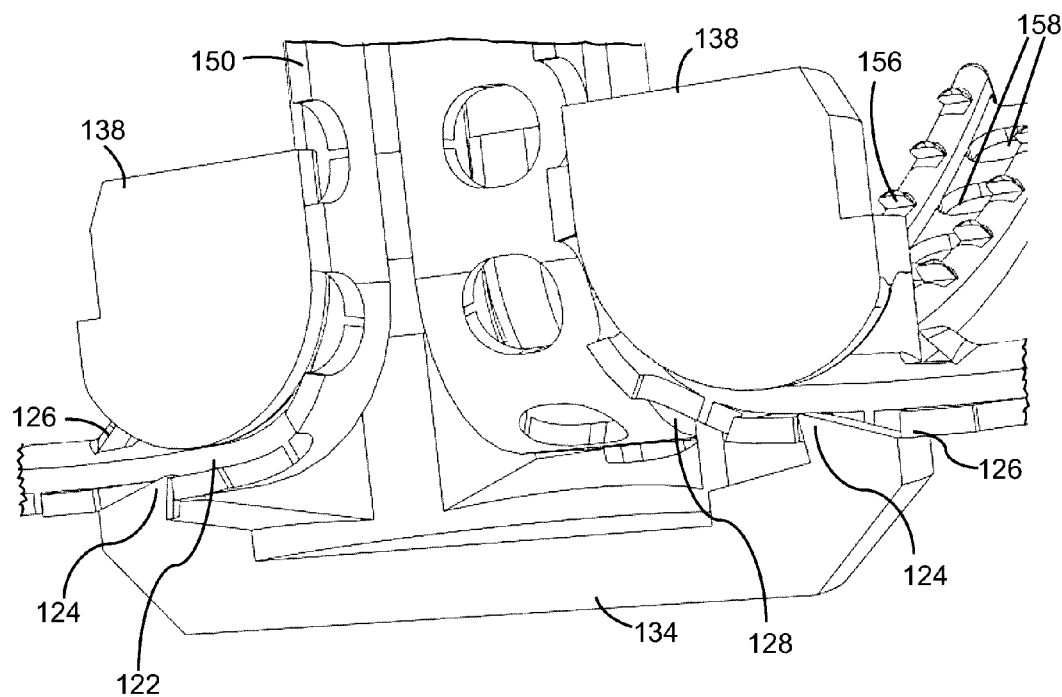
FIG. 14 is an enlarged view of a portion of the closure shown in the cross-section view of FIG. 13.
Figure 15:
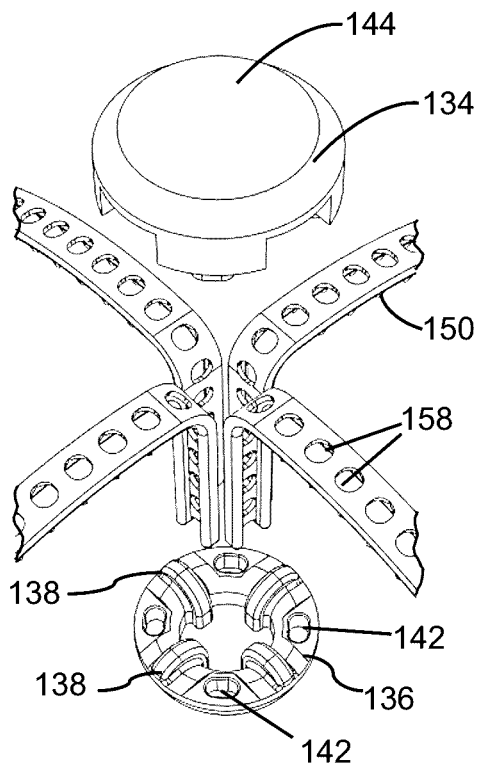
FIGS. 15 and 16 are exploded perspective views of the two piece head and portions of the arms of the trocar site closure of FIG. 2.
Figure 16:
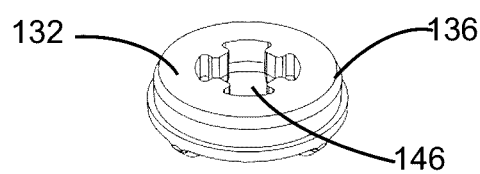
Figure 16:
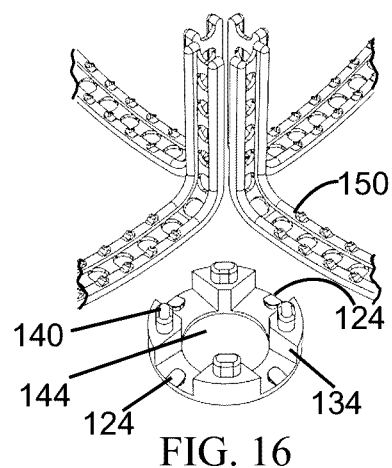

The trocar site closure 100, shown in FIGS. 2 and 13-16, is an alternate embodiment to the above described closure 10. While either head 20 of closure 10 or head 120 of closure 100 could be of unitary construction or have multiple components, head 20 is shown of unitary construction and head 120 is shown having two components, head first portion 134 and head second portion 136. Similar to closure 10, head 120 has passages 122 which each have a discontinuity 124 therein, each passage 122 having an exterior opening 126 and an interior opening 128. Arms 150 for closure 100 resemble straps with a plurality of openings 158 therethrough. Arms 150 have a distal end 152 and a proximal end 154. Arms 150 also have, as their grappling portion, a plurality of barbs 156 which extend from about the distal end 152 toward the proximal end 154 of arms 150. As shown in FIGS. 2, 13 and 14, arms 150 pass through passages 122 such that distal ends 152 extend outward from exterior openings 126 and proximal ends 154 extend upward through opening 146 in head second portion 136. Preferably, barbs 156 extend from about the distal end 152 toward exterior opening 126 when closure 100 is ready for insertion as shown in FIG. 2. As perhaps best shown in FIGS. 13 and 14, discontinuity 124 is in passage 122 and has a ramp like appearance. The lower portion of discontinuity 124 is toward the exterior opening 126 while the higher portion of discontinuity 124 is toward the interior opening 128. This configuration permits each arm 150 to be pulled from its proximal end 154 without interference from discontinuity 124. It is also envisioned that barbs 156 can be received into passage 122 without hindering movement of arms in an inward direction (i.e., in a direction that causes the distal ends 152 of arms 150 to be drawn closer to the head first portion 134). In contrast, if an arm 150 is pulled from its distal end 152, an opening 158 of arm 150 is received over discontinuity 124 and the higher portion of discontinuity 124 toward interior opening 128 will deter, and preferably prevent, that arm 150 from being pulled outward by the force exerted on its distal end 152. Discontinuity 124 in each passage 122 is on head first portion 134. Head first portion 134 has a closed end 144 (as best shown in FIG. 15) which helps protect the at least partially closed trocar opening. Between the portions of head first portion 134 containing the discontinuities 124 are upward extending pins 140, as shown in FIG. 16. Head second portion 136 includes a plurality of pin receptacles 142 which each receive an upward extending pin 140. Pins 140 and corresponding pin receptacles 142 mechanically lock together to form head 120. Alternatively a biocompatible adhesive can be employed to engage pins 140 and corresponding pin receptacles 142. Passage guards 138 are positioned on head second portion 136 and they help ensure proper alignment of the openings 158 on arms 150 with their respective discontinuity 124 in passage 122.

Closure 100 can be inserted into a trocar site opening in the body using an insertion device such as insertion device 80 shown in FIG. 3 and described above. As compared to head 20 which has its ring portion 30 received within opening 86 of body 82 and must be pushed out using movable inner sleeve 83, with head 120, it is envisioned that, by having the insertion device hold arms 150, head 120 can be simply held against the insertion end of the insertion device to be used. It is also envisioned that, instead of cutting and removing a portion of arms 50 with closure 10, portions of arms 150 toward their proximal ends 154 would preferably not be severed and removed. Instead, the entire closure 100 shown in FIG. 2 would preferably remain inside the patient's body at the location of the at least partially closed trocar site. Again, as with closure 10, closure 100 is preferably made of a biocompatible material.

Closure 10 discloses grappling portion 56 and closure 100 discloses barbs 156. Barbs 156 are shown extending along arm 150, which will facilitate grasping of the fascial layer over an enlarged surface area.

The closures 10 and 100 have been disclosed as preferably made from a bio-absorbable or bio-degradable material, which would be a biocompatible material capable of being absorbed or degraded within a patient without significant harmful effect. Such biocompatible materials are generally known to those skilled in the art. Examples are a commercially-available biodegradable polymer, such as, for example, polylactic-co-glycolic acid (PLGA), polycaprolactone (PCL), or similar polymers.

The trocar site closures 10, 100 can be scaled in size in order to function with any size trocar opening. The trocar site closures taught herein are used to at least partially close the trocar site opening. This could include even completely closing the opening. It is generally accepted that openings need to be reduced in size to about 6-8 mm to then close on their own. Sizing of the head, and/or possibly closing of an end of the head will also help block or at least partially block the opening. This will deter or prevent possible contaminants from entering the opening. In this case, contaminants include anything foreign, including tissues. The device also does not utilize any type of suturing technique, potentially avoiding adjacent muscle and nerve entrapment, which may lead to unnecessary post-surgery pain. It is envisioned that insertion devices, such as device 80, can be operated by a single user and, if desired, integrated with existing robotic surgical systems.

Disclosed herein are discontinuities 24, 124 in passages 22, 122, which permit movement of the arms inward, but deter or prevent outward arm movement. This directional movement bias action may be caused only by the discontinuity or by the discontinuity working in concert with the arm. In addition to what is taught with respect to closures 10 and 100, directional bias may be created by a configuration similar to that of a cable tie, where the arms include ridges that slope in a single direction and the openings include pawls. As an arm is retracted, the pawl rides over the slopes of the ridges. The pawl engages the reverse, non-sloped side of the ridge, preventing extension of the arm. In other embodiments, a ratchet and pawl structure may be used to create the directional bias. Other means for creating directional bias may also be used. All of the things disclosed in this paragraph function as a locking mechanism.

The grappling portions, such as 56, 156 taught herein, are configured to securely engage tissue. The grappling portions may include barbs, hooks, teeth, or other protrusions designed to engage tissue. All of the things disclosed in this paragraph function as a tissue engaging mechanism.

Both apparatus 10 and apparatus 100 are shown having four arms 50, 150. In other embodiments, the device may include two, three, five, six, or more arms. Preferably, the apparatus includes at least two arms.

While the disclosed trocar site closure apparatuses and insertion device have been discussed primarily in terms of use in hernia prevention at trocar sites following laparoscopic surgeries, it should be understood that the device can be used to at least partially close openings in a patient's body and block tissue passage into the openings regardless of whether the openings were created by a trocar or other instrument, or whether the openings were created intentionally or by accident.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:
1. A trocar site closure system, comprising:
   a trocar site closure including:
   a. a head, said head having a plurality of arm receiving passages therethrough, each of said plurality of arm receiving passages having a discontinuity therein;
   b. a plurality of arms, each of said plurality of arms having a distal end and an opposed proximal end, each said arm having a grappling portion;
   c. each of said plurality of arms is received by one of said plurality of arm receiving passages, and where said discontinuity in each said arm receiving passage permits movement of said arm received when said arm is pulled from said proximal end, but where said discontinuity in each said arm receiving passage deters movement of said arm received when said arm is pulled from said distal end;
   wherein each said arm receiving passage is from an exterior opening in said head to an interior opening in said head and where said arm received in said arm receiving passage has a portion terminating in said distal end extending from said exterior opening and a portion terminating in said proximal end extending from said interior opening; and
   wherein each said discontinuity is a ramp, said ramp sloping upward from a location toward said exterior opening in said head to a location toward said interior opening in said head.

2. The trocar site closure system of claim 1 where said grappling portion is at least on the portion of said arm extending from said exterior opening.

3. The trocar site closure system of claim 2, where said grappling portion is toward said arm distal end.

4. The trocar site closure system of claim 2, where said grappling portion is along said arm from said distal end toward said exterior opening in said head.

5. The trocar site closure system of claim 4, where said grappling portion comprises a plurality of barbs.

6. The trocar site closure system of claim 1, where each of said plurality of arms have a plurality of openings therein, where at least one of said openings can engage said ramp contained in said passage through which said arm passes.

7. The trocar site closure system of claim 1, where said head and said plurality of arms are made of a biocompatible material.

8. The trocar site closure system of claim 1, where said head is of unitary construction.

9. The trocar site closure system of claim 1, where said head has a first portion and a second portion, said first portion having said discontinuities thereon, said second portion having passage guides thereon, said passage guides being positioned opposite said discontinuities.

10. The trocar site closure system of claim 1, where each of said plurality of arms have a plurality of openings therein, where at least one of said openings can engage said ramp contained in said passage through which said arm passes.

11. The trocar site closure system of claim 10, where said grappling portion is along said arm from said distal end toward said exterior opening in said head.

12. The trocar site closure system of claim 11, where said grappling portion comprises a plurality of barbs.

13. The trocar site closure system of claim 1, where said head has a top portion and a top open end, and where said arm portion terminating in said proximal end extending from said interior opening extends further through said top open end.

14. The trocar site closure system of claim 13, where said head top portion removably abuts an insertion end of a body of an insertion device and where said arm portions extending through said top open end and terminating in said proximal end are removably received within said insertion end of said body.

15. The trocar site closure system of claim 14, where said insertion device includes a control mechanism, said control mechanism operably linked to said arm portions removably received within said insertion end of said body such that said arm portions can be pulled upward in said body of said insertion device to decrease a length of said arms extending from said head exterior openings to said distal ends.

16. The trocar site closure system of claim 15, where said head has a ring portion at said top portion, said ring portion being removably received within said insertion end of said insertion device body.

17. The trocar site closure system of claim 16, where said insertion device body has an inner sleeve therein, where said inner sleeve is operable to expel said ring portion from said insertion end of said insertion device body.

18. The trocar site closure system of claim 1, where said head is sized to deter contaminants from entry into a trocar site.

19. The trocar site closure system of claim 1, where said head has a closed end which deters contaminants from entry into a trocar site.

\* \* \* \* \*